US00PP11346P

United States Patent [19]

Verwer

[11] Patent Number: Plant 11,346

[45] Date of Patent: Apr. 11, 2000

[54] DAHLIA PLANT NAMED 'KARMA LAGOON'

[75] Inventor: Aad Verwer, Lisse, Netherlands

[73] Assignee: Fa. Gebr. Verwer, Lisse, Netherlands

[21] Appl. No.: 09/026,012

[22] Filed: Feb. 19, 1998

[51] Int. Cl.[7] ..... A01H 5/00

[52] U.S. Cl. ..... Plt./321

[58] Field of Search ..... Plt./321

[56] References Cited

PUBLICATIONS

GTITM UPOVROM Citation for 'Karma Lagoon' As per NL PBR DHL0054; Mar. 27, 1995.

GTITM UPOVROM Citation for 'Karma Lagoon' As per QZ PBR 960406; Mar. 25, 1996.

*Primary Examiner*—Howard J. Locker
*Assistant Examiner*—Kent L. Bell
*Attorney, Agent, or Firm*—Christie, Parker & Hale, LLP

[57] ABSTRACT

A dahlia plant variety producing purple/violet flowers.

1 Drawing Sheet

BACKGROUND OF THE INVENTION

The present invention relates to a new and distinct variety of *Dahlia hybrida* known by the varietal denomination 'Karma Lagoon'. The female parent of 'Karma Lagoon' is a variety known as 'Stratos' and the male parent is the variety known as 'Claudette', both of which are not known to be patented.

SUMMARY OF THE INVENTION

The new variety is a dahlia plant useful for growing outdoors and under glass which produces attractive purple/violet flowers on long stems. Among the traits possessed by the new variety which in combination distinguish it from other varieties known to the inventor are its attractive flowers borne on long stems.

Asexual reproduction by cuttings of the new variety in The Netherlands has demonstrated that the combination of characteristics as described herein for 'Karma Lagoon' are firmly fixed and are retained through successive generations of asexual reproduction.

COMPARISON WITH PARENTS

The new variety differs from its parents in flower color.

BRIEF DESCRIPTION OF ILLUSTRATION

The accompanying color photographic illustration shows a typical bloom of the new variety in colors as nearly true as possible with an illustration of this type.

DESCRIPTION OF THE NEW VARIETY

In the following description, color references are to The Royal Horticultural Society Colour Chart, where color values refer to color plate numbers in this chart.

The following observations are of plants described and grown in The Netherlands under outdoor conditions which approximate those generally used in commercial practice.

'Karma Lagoon' has not been observed under all possible environmental conditions. The phenotype may vary with variations in environment such as temperature, light intensity, day length and cultural conditions.

Parentage:

*Female parent.*—'Stratos'.

*Male parent.*—'Claudette'.

Plant:

*Form.*—Upright, spreading.

*Height.*—About 80 cm.

*Branching characteristics.*—Moderate.

*Flower stem.*—Strong, straight. Length: About 60 to 70 cm. Color: Near 187A.

*Hardiness.*—Plants are winter hardy to 0° C.

*Natural flowering season.*—July to November in The Netherlands under glass.

*Disease resistance.*—Similar to the species.

*Foliage.*—Quantity: Many. Size of leaf: Compound leaflet leaf length about 22 cm, width about 13 cm; single leaf length about 8.7 cm, width about 4.9 cm. Shape of leaf: Ovate, apex is acute, base is acute. Leaf edge: Juvenile leaf margin is Entire, mature leaf margin is Dentate. Texture: Leaf upperside: Leathery. Leaf under side: Smooth. Color: Leaf upperside: Near 137A. Leaf under side: Near 191A. Venation: Pinnate. Petiole length: Terminal, about 10 cm, lateral about 5 cm. Stipules: None. Stem color: Near 187A.

*Sepals.*—Number: About 35. Length: About 1.9 cm. Width: About 1.5 cm. Color: Near 137A. Base: Rounded. Apex: Broadly acute.

Bud:

*Form.*—Globular.

*Size.*—About 1 cm.

*Opening rate.*—About 14 to 20 days.

*Color of ray florets.*—When sepals first divide near 80B; when ray florets begin to unfurl near 80B.

Flower:

*Inflorescence.*—Blooms borne singly. Bloom form: Decorative. Bloom diameter: About 12 cm. Flowering: About 2 to 3 main branches are produced, with flowering occurring 35 to 40 days later.

*Color tonality from a distance.*—Violet/blue.

*Lasting quality.*—About 20 days on plant; about 7 to 9 days after cutting.

*Ray florets.*—Length: About 5.8 cm. Width: About 2.1 cm. Shape: Oblong. Apex: Obtuse. Base: Rounded. Color: Purple/violet. Inner ray florets (upper surface and undersurface): Near 80B. Outer ray florets (upper surface and undersurface): Near 80B. Point of ray floret attachement: Near 80C. As bloom ages: Colors fade to near 78C tones. Fragrance: None.

*Disc florets.*—Number: About 20. Length: About 1.3 cm. Color: Near 7A. Shape: Cylindric.

Reproductive organs:

*Stamens.*—Near 17A.

*Anthers.*—About 2 mm, near 17B.

*Pollen.*—Near 12A.

*Pistils.*—Styles divided, near 12A; stigmas near 12A.

*Character of ovaries.*—1 per pistil.

I claim:

1. A new and distinct dahlia plant of the variety substantially as shown and described.

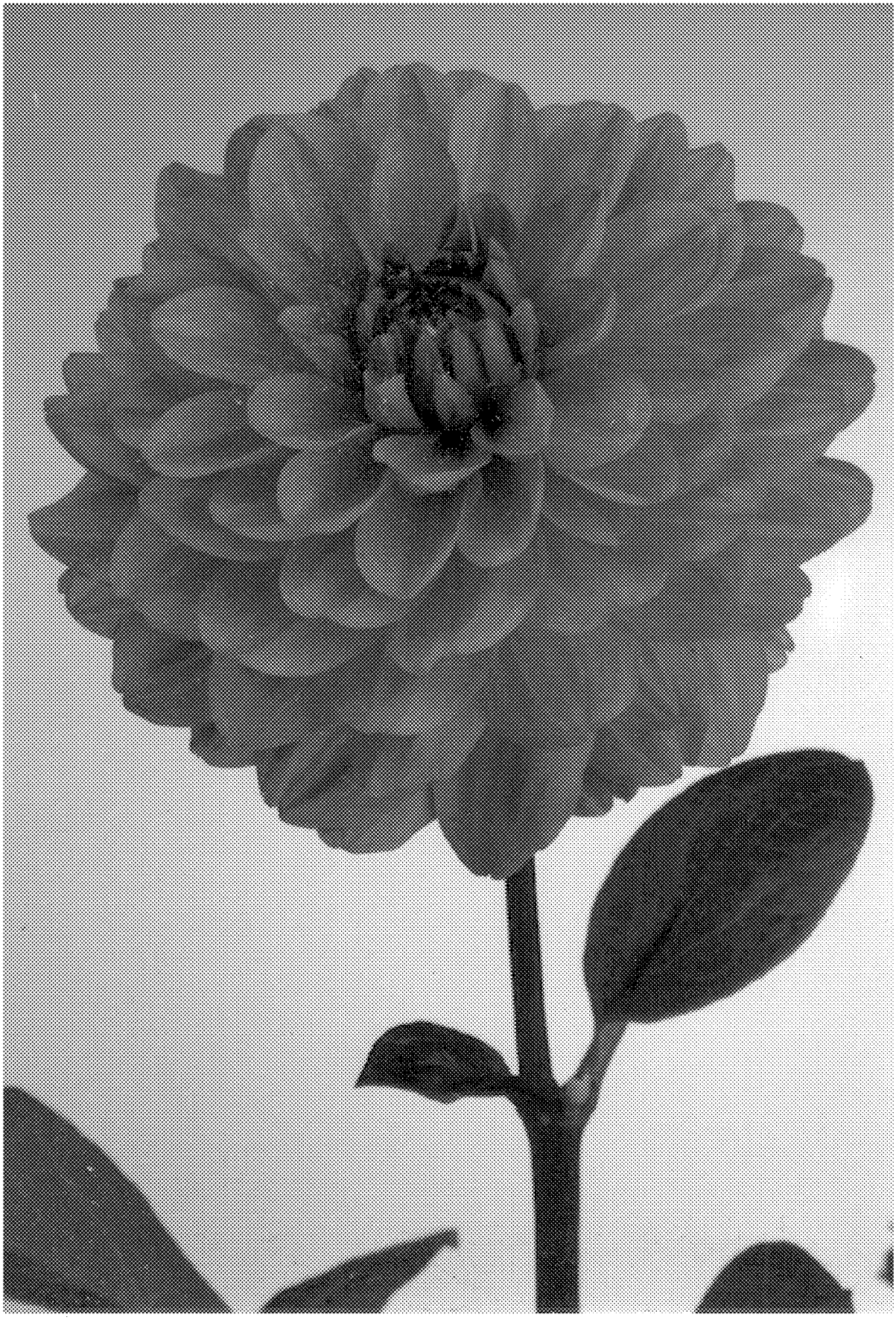

* * * * *